(12) United States Patent
Roth et al.

(10) Patent No.: US 6,323,413 B1
(45) Date of Patent: Nov. 27, 2001

(54) MICROTUBING WITH INTEGRAL THERMOCOUPLE

(75) Inventors: Ronald B Roth, Signal Mountain; E. William Darby, Chattanooga, both of TN (US)

(73) Assignee: HV Technologies, Inc., Trenton, GA (US)

( * ) Notice: Subject to any disclaimer, the term of this patent is extended or adjusted under 35 U.S.C. 154(b) by 0 days.

(21) Appl. No.: 09/296,137

(22) Filed: Apr. 21, 1999

Related U.S. Application Data

(60) Provisional application No. 60/082,693, filed on Apr. 22, 1998.

(51) Int. Cl.[7] ............................................. H01L 35/00
(52) U.S. Cl. ............................................. 136/201; 136/228
(58) Field of Search ............................................. 136/228, 201

(56) References Cited

U.S. PATENT DOCUMENTS

| | | | |
|---|---|---|---|
| 4,051,284 | * 9/1977 | Ohkubo et al. | 428/36 |
| 4,411,266 | * 10/1983 | Cosman | 128/303.18 |
| 4,484,018 | * 11/1984 | McLynn | 136/230 |
| 4,732,619 | * 3/1988 | Nanigian | 136/228 |
| 4,966,597 | * 10/1990 | Cosman | 606/50 |
| 5,111,002 | * 5/1992 | Hollander | 174/102 P |
| 5,464,485 | * 11/1995 | Hall | 136/230 |
| 5,533,987 | * 7/1996 | Pray | 604/280 |
| 5,620,479 | * 4/1997 | Diederich | 607/97 |
| 5,677,484 | * 10/1997 | Stark | 73/204.24 |
| 5,888,436 | * 3/1999 | Keith et al. | 264/103 |

* cited by examiner

Primary Examiner—Kathryn Gorgos
Assistant Examiner—Thomas H Parsons
(74) Attorney, Agent, or Firm—Miller & Martin LLP

(57) ABSTRACT

A novel microtubing and a method of manufacture is provided. The resulting microtubing has at least two thermo-elements separated by a resin layer except in defined areas where the insulating resin layer is selectively removed. The resulting microtube provides improved performance, reduced size, increased flexibility, and can be efficiently manufactured.

30 Claims, 4 Drawing Sheets

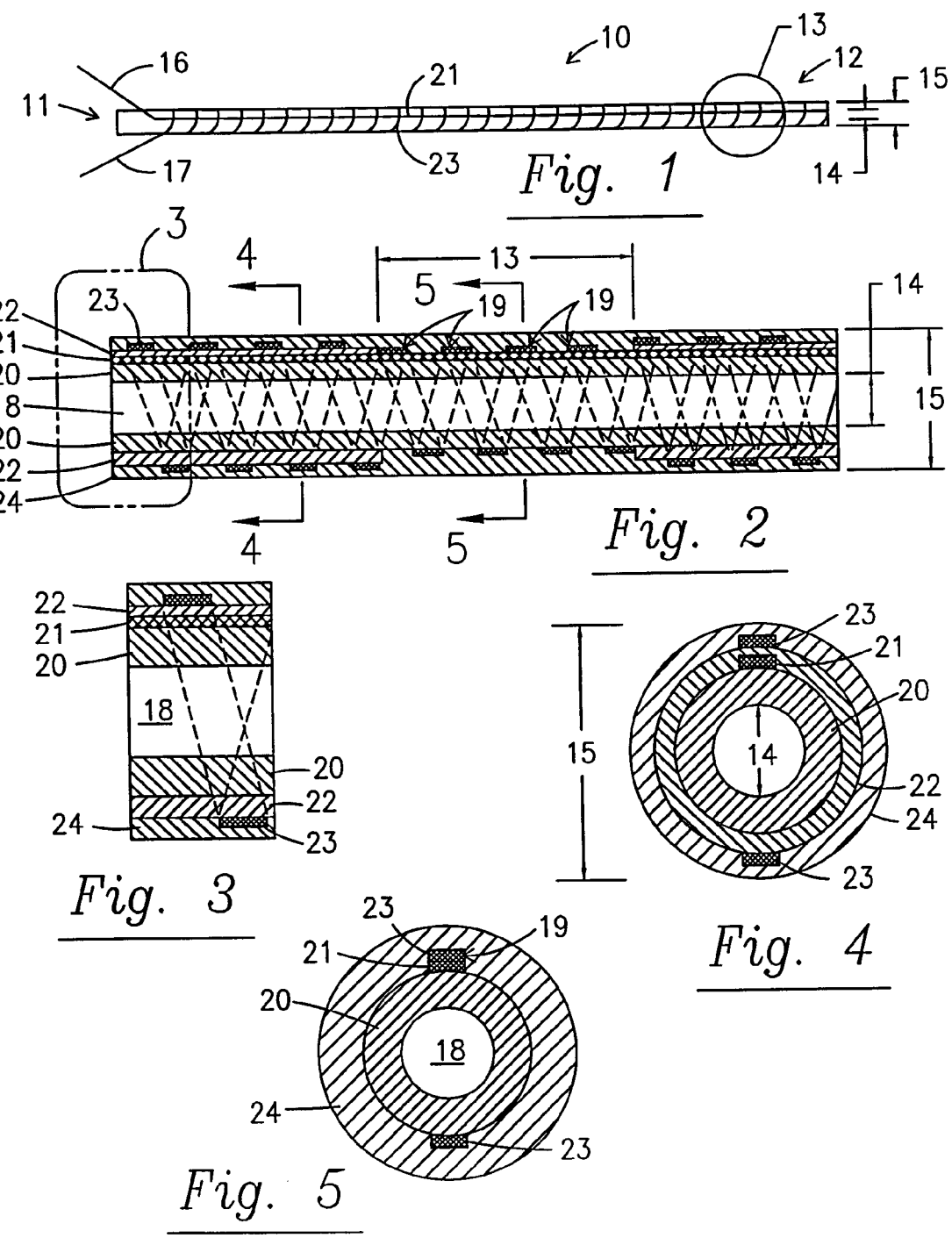

MICROTUBING WITH INTEGRAL THERMOCOUPLE

This application claims the benefit of U.S. Provisional Patent application Ser. No. 60/082, 693, filed Apr. 22, 1998.

BACKGROUND OF THE INVENTION

1. Field of the Invention

The present invention relates to a flexible tubular product with an interior lumen and a thermocouple imbedded in the wall of the product. Utilizing the disclosed methods of manufacture, tubular products can be manufactured with thin walls and outer diameters of only about 0.020 inches rendering the resulting microtubing suitable for use as a catheter component in medical applications. In some circumstances, the lumen may be filled with a guide wire or otherwise not be used for communication of fluids. The lumen may also be formed over a hypotube.

2. Description of the Related Art

Thermocouple temperature sensors require the junction of two dissimilar conductors. As utilized herein, a "thermoelement" is one conductor of a pair of dissimilar conductors which may be used to form a thermocouple. A "thermocouple pair" comprises two thermoelements made of different thermoelectric materials.

In many medical applications, it is desirable to place a thermocouple within a patient's body. Thermocouples can not only be used to measure temperatures during electrosurgical procedures and in other localized areas of a patient's body, but thermocouples can be used as a part of flow measurement devices and other metering systems to report on bodily functions.

In designing a medical apparatus, it is a continual goal to produce smaller and "smarter" instrumentation to permit greater flexibility in the performance of medical procedures. In addition, cost reduction is a goal in all manufacturing processes. Also, reducing the size and form factor of the resulting microtubing is a goal. Furthermore, the manufacture of other devices required time consuming hand assembly of components. The present invention allows for the manufacture of integrated single and multiple integrated thermocouples within the wall of a microtube.

SUMMARY OF THE INVENTION

The present invention provides a tubular type product with an open lumen suitable for use as a catheter with at least one thermocouple imbedded in the wall of the tubing. The inner diameter of the product will typically range from about 0.005 and 0.2 inches and the wall thickness will range from about 0.004 to 0.01 inches. The product is manufactured utilizing an automated continuous process which is preferable for products of small dimensions, and only a small amount of manual finishing work is required.

It is therefore a purpose of the invention to provide a smaller, more flexible, thinner walled catheter tube with an imbedded thermocouple than has heretofore been available.

It is another object of the invention to provide an automated manufacturing process for use in producing microtubing with an imbedded thermocouple.

It is yet another object of the invention to produce a flexible thermocouple less than about 0.1 inches in diameter, and preferably less than 0.09, 0.05, and 0.02 inches in diameter.

It is yet another object of the invention to provide at least one embodiment of a microtubing with multiple thermocouples imbedded in the tubing wall.

It is another objective of at least one embodiment to provide a single thermocouple in the wall that has been manufactured such that "backup" thermocouple joints exist such that if the primary joint should no longer be in contact, another nearby thermocouple joint takes effect.

Still another objective of at least one embodiment is to provide N thermocouples integrated into microtubing that are 360/N degrees apart (e.g., if N=2, the thermocouples are 180 degrees apart).

Another objective of one embodiment having multiple thermocouples is to provide multiple thermocouples that are evenly spaced apart from one another in a precise manner.

Another objective of one embodiment is to provide a thermocouple integrated microtubing in which a strain relief lead connection or reference junction does not occur on the microtubing itself. This may minimize the resulting complexity and profile of the microtubing.

Another objective of the present invention is to provide a thermcouple integrated microtubing having a resulting time constant of less than about 100 milliseconds.

Another objective of an embodiment having multiple thermocouples is the use of a common negative lead wire in which N thermocouples result from N+1 wires.

These and other objects of the invention will become apparent in reviewing the features fully described and particularly pointed out in the claims, the following description and drawings setting forth certain illustrative, but not exclusive, embodiments of the invention.

BRIEF DESCRIPTION OF THE DRAWINGS

FIG. 1 is a simplified side plan view of microtubing with an imbedded thermocouple according to the present invention.

FIG. 2 is an enlarged sectional side plan view of the thermocouple region of the microtubing of FIG. 1;

FIG. 3 is an enlarged sectional side plan view 3—3 of a section of the microtube of FIG. 2 outside the thermocouple region;

FIG. 4 is an enlarged sectional end view along line 4—4 of the microtubing of FIG. 2 outside the thermocouple region; and FIG. 5 is an enlarged sectional end view of the microtubing within the thermocouple region.

DETAILED DESCRIPTION OF THE DRAWINGS

Figure 6:
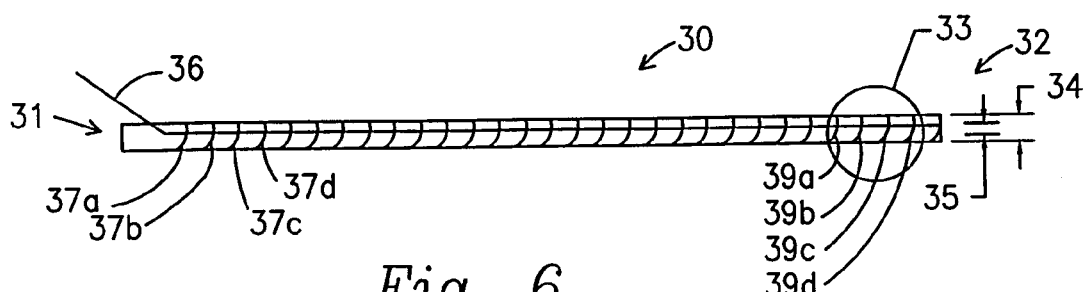
FIG. 6 is a simplified side plan view of microtubing with multiple imbedded thermocouples according to the present invention.

A microtube 10 with integral thermocouple 19 is shown in FIG. 1 with proximal end 11, distal end 12, and thermocouple zone 13. Also shown are a first thermoelement in the form of wire 21 which proceeds straight down the length of the microtube 10, and second thermoelement in the form of wire 23 which is helically coiled about the microtube. Exposed end 16 of first wire 21 and exposed end 17 of second wire 22 can be connected to the desired thermocouple circuitry of conventional design. The inner diameter 14 of microtube 10 is preferably between about 0.005 and 0.2 inches. The wall thickness is preferably on the order of 0.004 to 0.01 inches resulting in the microtubing outer diameter 15.

FIG. 2 shows an enlarged view of the thermocouple zone 13 of microtube 10. In particular, the lumen 18 is shown together with the first wire 21, second wire 23, first resin layer 20, second resin layer 22 and third resin layer 24. FIG. 3 provides a detailed view of these components outside the thermocouple zone 13.

In practice, a microtube 10 is preferably manufactured on a wire mandrel of oxidized copper, stainless steel or silver plated copper. Optionally, the integrated thermocouple in a microtube may be manufactured on a stainless steel hypotube. The stainless steel hypotube preferably remains part of the final assembly and is not removed. First, the inner layer 20 is coated onto the mandrel, utilizing the techniques described in Ohkubo, U.S. Pat. No. 4,051,284 and U.S. Pat. No. 5,888,436. Coatings may also be extruded or applied in any other manner known in the art as well. The inner layer 20 will preferably be PTFE, FEP, or if an oxidized copper mandrel is used, polyimide. It will be understood that more than one layer of resin may be applied to form the inner layer 20 and the composition and thickness of the inner layer 20 may be varied over the length of the mandrel as described in U.S. Pat. No. 5,888,436, to impart desired characteristics to the resulting microtube. It will also be understood that if FEP or PTFE is utilized, those materials should be etched to improve bonding with subsequent layers. It will also be understtod that if FEP or PTFE is utilized, these materials may be etched on the outer diameter (OD) to improve bonding with subsequent layers.

After the inner layer 20 is complete, a first thermoelement is attached. In the accompanying figures, this thermoelement, wire 21, is straight and attached by "glueing" the wire on a continuous basis to the first layer 20. This is accomplished by coating the first wire 21 with the resin selected for the second layer 22 and bonding the coated wire to the first layer 20. Alternatively, the first wire 21 may be helically wound over the first layer 20. In the case of winding of the first thermoelement, precoating of the material for the second layer 22 is optional. It will be understood that if the first thermoelement is wound about the microtubing, the winding direction and spacing will affect the frequency with which the first thermoelement intersects the later added second thermoelements.

In the next manufacturing step a second resin layer 22 is applied. The second resin layer 22 performs an insulating function and separates first wire 21 and second wire 23 in the sections of the tubing 10 that are not in the thermocouple zone 13, as shown in FIGS. 3 and 4. It is preferable that the second resin layer be a different color from the combination of the first resin layer 20 and the third resin layer 24. Typically the second resin layer is colored with a small amount of dye, usually black, however other colors may be utilized for this purpose. As described below, this coloring facilitates visual identification of the thermocouple zone 13. Suitable materials for the second resin layer 22 include: polyimide, polyurethanes, PVDF (Kynar), polyester, and polyamides.

Figure 10:
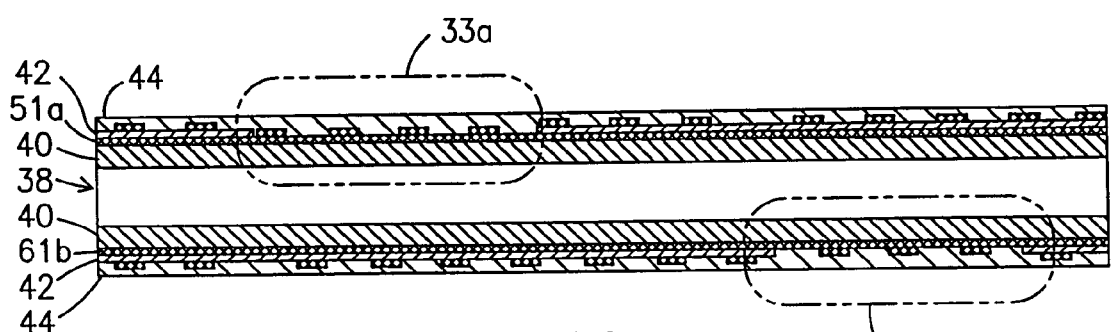
FIG. 10 is an enlarged sectional side plan view of microtubing with multiple embedded thermocouples and a plurality of first thermoelements.

After the second resin layer 22 is applied, the first wire 21 is exposed on a periodic basis depending upon the desired length of thermocouple imbedded microtubing 10 to be manufactured. Typical lengths of microtubing for catheter use would be approximately three to five feet. At these periodic intervals, the first wire 21 is exposed by removing the second resin layer 22 in selected regions, as by chemical machining, thereby creating discontinuities in the insulation of the first wire. For a polyimide resin such chemical machining would typically involve the use of a heated strong base solution with pH of about 14 such as a sodium hydroxide solution or a strong heated acid with a pH of about 1. A preferred solution is 956 ML Stripper available from Fidelity Chemical Company, or equivalents. Alternatively, laser machining or conventional machining such as centerless grinding may be employed. Conventional machining would be most appropriate if first thermoelement wires were spaced apart on the sides of the microtubing, as on opposite sides, and it was desired to remove the second resin layer from only one of the first thermoelement wires at a particular location as shown in FIG. 10. The length of the second resin layer 22 that is removed will typically depend upon the frequency with which the first 21 and second 23 thermoelements intersect. Generally, at least two intersections of the thermoelements will be exposed, so that if the second thermoelement is a helically wound wire 23, with the usual number of windings of between about 5 and 150 per inch, then about 0.02 to 1.0 inch of the second resin layer 22 will be removed. Typical winding frequency will be on the order of 10–15 per inch, but in order to impact the stiffness, strength, or other tubing characteristics, the broader winding range described above may be employed.

Next, the second wire 23 is attached. Typically, second wire 23 will be coiled around the microtube, although multiple wires may be used, or if the first thermoelement 21 has been coiled, the second wire 23 may be attached straight, coiled at a different winding frequency or wound in reverse direction to affect the frequency of possible thermocouple junctions and the characteristics of the tubing. So long as first wire 21 and second wire 23 intersect at regular or determinable locations over the length of the microtube, the wires may be attached or wrapped about the microtube 10 in a variety of ways. It will be understood that first wire 21 and second wire 23 are selected largely for their properties in forming a thermocouple. Specifically suitable thermoelement materials are set forth in Table I below:

TABLE I

THERMOCOUPLE WIRE PAIR COMBINATIONS

| Thermocouple Type (ANSI Code) | Initial Thermoelement Material (positive lead) | Complementary Thermoelement Material (negative lead) |
| --- | --- | --- |
| J | Fe | Cu—Ni |
| K | Ni—Cr | Ni—Al |
| T | Cu | Cu—Ni |
| E | Ni—Cr | Cu—Ni |
| N | Ni—Cr—Si | Ni—Si—Mg |
| R | Pt - 13% Rh | Pt |
| S | Pt - 10% Rh | Pt |
| B | Pt - 30% Rh | Pt - 6% Rh |
| G | W | W - 26% Re |

TABLE I-continued

THERMOCOUPLE WIRE PAIR COMBINATIONS

| Thermocouple Type (ANSI Code) | Initial Thermoelement Material (positive lead) | Complementary Thermoelement Material (negative lead) |
|---|---|---|
| C | W - 5% Re | W - 26% Re |
| D | W - 3% Re | W - 25% Re |

When second wire 23 is attached to the microtube, a thermocouple joint 19 is formed where the first wire 21 and second wire 23 are in contact. Such contact should occur only in those areas where first wire 21 was exposed by selective removal of the second resin layer 22.

Finally, a third resin layer 24 is applied. This third resin layer 24 is often a structurally stiff material to ensure that the thermocouple joint is reliable for the life of the product. Suitable materials for the third resin layer 24 include polyimide, FEP, polyurethane, PVDF (Kynar), polyester, polyamide, and other materials (both as coatings and extrusions). Because of the color difference of the second resin layer 22, the selective removal of second resin layer 22 in the thermocouple zone 13 causes a distinct color difference when comparing the thermocouple zone 13 to the remainder of the microtubing 10.

Thus, one preferred embodiment of this patent is for the thermocouple joint 19 to be held together, at least partially, by the third resin layer 24. Advantages of this method include: (1) it is easy to manufacture and (2) the size of the thermocouple joint 19 is smaller than that which maybe achieved either by soldering with a dissimilar material and/or welding. However, soldering and/or welding to create a thermocouple joint 19 in this manufacturing process may be utilized.

To finish the thermocouple imbedding microtubing, each individual thermocouple zone 13 is located, the microtubing is cut to a gross manufacturing length and the mandrel is removed, the lead wires 16 and 17 are exposed, and the microtubing is then cut to the net length desired for the finished product.

Since the manufacturing process may be performed nearly continuously, the wires utilized as thermoelements may be extremely small. The small thermoelement wire sizes and thin wall nature of the manufacturing process have been found particularly effective at creating a thermocouple with an exceedingly fast response time. This allows transient temperature conditions to be measured for those applications which require such characteristics (e.g., electroablation of tissue and tumors which are common in the field of minimally invasive surgery).

EXAMPLES

A first resin layer 20 of natural colored polyimide is coated onto an oxidized copper mandrel of 0.018 inch diameter. The thickness of this layer is approximately 0.002 inches and requires coating the mandrel approximately 18 to 20 times.

This layer thickness could be thinner, but the catheter wall thickness at the proximal end of the catheter 11 consists only of this layer at the location where the thermocouple leads 16, 17 are exposed. The thickness of the first resin layer may provide needed support at this proximal end. A first thermoelement 21 in the form of 0.001 inch by 0.005 inch flat Alumel wire 21 is then attached with a black dyed polyimide 22 to the first resin layer 20.

The overcoat thickness of the resin layer 22 over the Alumel wire is approximately 0.001 inches and requires 8 to 10 coating passes. To obtain the black color, 1.5% by weight carbon black is added to the polyimide enamel.

The second layer 22 is then chemically machined periodically by using Fidelity Chemical P/N 956 ML Stripper for a length of 0.25 inches every 60 inches, to expose the first Alumel wire thermoelement 21 in these machined regions.

The coated mandrel is then passed through a single ended coiler which helically winds a second thermoelement comprised of a 0.001"×0.004– flat Chromel wire 23. This second thermoelement wire is wrapped around the mandrel at a period or frequency of 10 to 15 wraps per inch. This enables the Chromel wire to come into contact with Alumel wire approximately 5 times in each machined region to ensure intimate contact. The actual thermocouple joint 19 is the contact point between the first or most proximal Chromel wire and Alumel wire.

This method results in a very robust thermocouple design: to achieve a "good" thermocouple joint, only one out of the five contact points must be intimate. In addition, if one of the contact points should "fail," a backup contact joint already exists in the design construction.

Durability may be provided by a third resin coating 24 of natural polyimide applied with a wall thickness of 0.001 inches. This requires coating the mandrel 8 to 10 times. Due to the slight variation of the outside diameter of this system, a reduced polyimide enamel viscosity is utilized to prevent blistering.

Each tubing segment is realized by: (1) removing the mandrel by exposing the mandrel on each end of the catheter, stretching the mandrel 20 to 30 percent, and sliding it out; (2) removing the copper oxide by flushing with nitric acid; and (3) cutting the microtubing into lengths of 48 inches. At the proximal end of the tubing, the wire elements are exposed and connected to a thermocouple meter. The resulting microtubing had an inner diameter of 0.0180 inches and a maximum outer diameter of 0.030 inches. Due to the small wires and thin polyimide walls utilized in the design, the thermocouple had a time constant of approximately 80 milliseconds.

Figure 7:
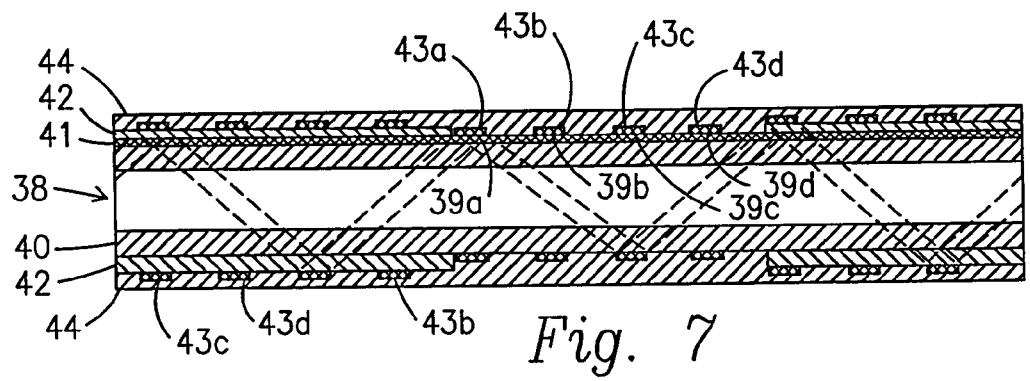
FIG. 7 is an enlarged sectional side plan view of the thermocouple region of a multiple thermocouple microtubing with regular thermocouple spacing.

An improved variation of the invention permits the manufacture of microtubing with multiple thermocouples. FIG. 6 shows a simplified side plan view of microtubing 30 with multiple thermocouples 39a, 39b, 39c, 39d. Such multiple thermocouple microtubing 30 is manufactured in a fashion quite similar to the microtubing 10 with a single thermocouple shown in FIG. 1 where elements "31", "32", "33", "34", and "35" correspond to elements "11", "12","13", "14", and "15". Specifically, a mandrel is selected and a first layer 40 (shown in FIG. 7) of resin is coated onto the mandrel. Then a first wire 41 selected of an appropriate thermoelement material is attached to the microtubing, utilizing a second resin material that will also form a second layer 42 of the microtubing. A sufficient insulating thickness of the second layer 42 of resin must be coated over the first wire 41 to prevent accidental shorting of wire 41 to any of the second thermoelement wires 43a, 43b, 43c, 43d which are attached in a subsequent step.

As previously discussed in connection with the single thermocouple microtubing 10, it is desirable that the second layer of resin material 42 be of sufficiently different color from the first layer 40 and third layer 44 to permit easy thermocouple identification. Typically the second layer of resin material 42 is colored with a black dye. After the second layer of resin material 42 has been coated over the first thermoelement 41, selective portions are removed and second thermoelement wires 43a, 43b, 43c, 43d are attached as by helical winding or other method over the microtube. This results in the formation of thermocouples 39a, 39a, 39b, 39c, 39d at the locations where the second resin layer has been removed. Finally, a third resin layer 44 is coated or extruded over the first two layers 40, 42 and thermoelements 41 and 43. Typically this third layer 44 is structurally stiff to ensure that the thermocouple joints 39 are reliable for the life of the product. Because of the removal of the second layer 42 in the thermocouple region there is a distinct color difference between the thermocouple location and the remainder of the tubing. Finally, each individual thermocouple is located, the internal mandrel is removed creating a lumen 38, microtubing is cut to length, and the lead wires 36 and 37a, 37b, 37c, 37d are exposed for connection to the appropriate thermocouple circuitry. It will be understood by reference to the simple schematic drawing in FIG. 9 that the number of thermocouples is not limited to the four illustrated in FIG. 6, but can be generalized to the case of n distinct thermocouples. In one construction, thermocouples would be evenly spaced in order to effectively provide temperature readings over a designated length. For instance, if 8 second thermoelement wires 43 were utilized and wound in a fashion that left the resulting thermocouples 39 spaced about 0.75 inches apart, the resulting microtubing could be utilized as a catheter component that would provide temperature readings over a six inch length.

Figure 8:
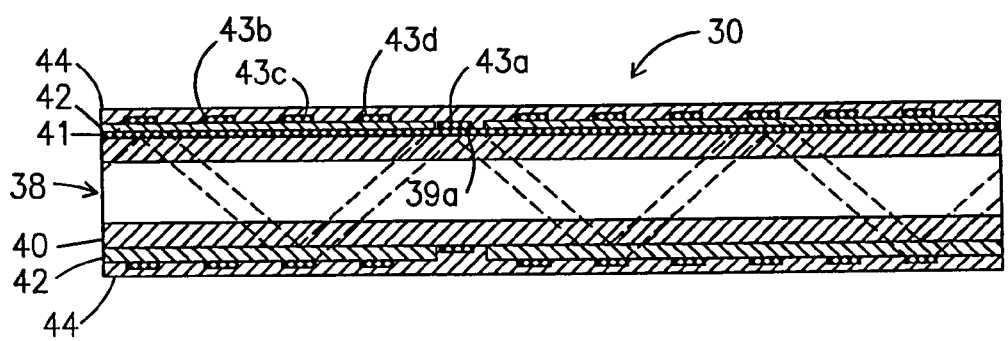
FIG. 8 is an enlarged sectional side plan view of a multiple thermocouple microtubing with selective thermocouple spacing.

Alternatively, a microtubing with embedded thermocouples might be constructed along the lines illustrated in FIG. 8, where the portion of the second resin layer 42 removed is sufficiently narrow that only a single second thermoelement wire 43a is permit to form a thermocouple 39a with first thermoelement wire 41 at a designated location along the length of the microtube 30. This technique requires greater precision in the machining of the second resin layer 42 to expose only relatively short segments of the first thermoelement wire 41. Utilization of this technique requires precision spacing and winding technology for thermoelement location.

Figure 9:
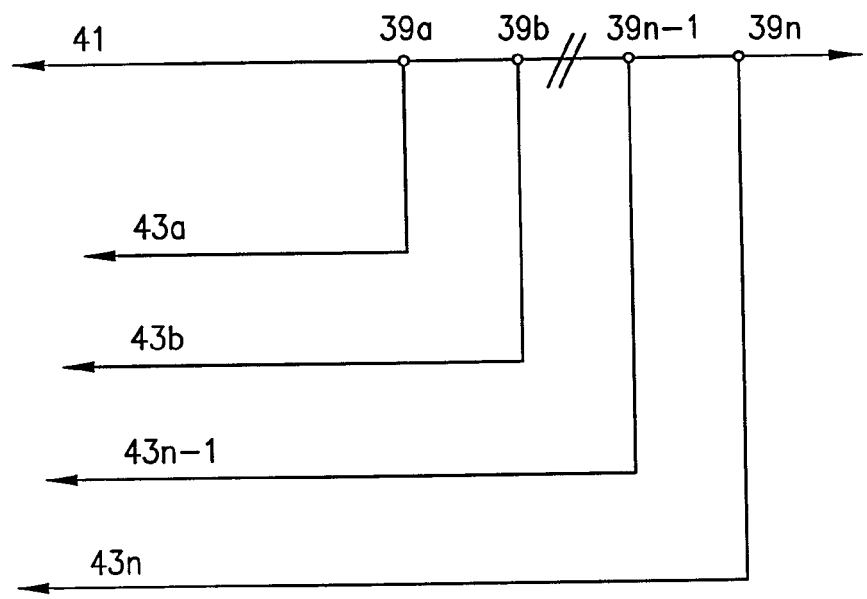
FIG. 9 is a simplified electrical schematic showing the formation of N thermocouples by N+1 thermoelements.

FIG. 10 shows another variation of a multiple thermocouple microtubing construction, with two separate first thermoelement wires 51a, 51b located on opposing sides of the microtube. As illustrated in FIG. 10, the second resin layer 42 is selectively removed in thermocouple zone 33a and 33b to expose only one of the first thermoelement wires 51a or 51b at a given longitudinal section of the microtube. Techniques may be utilized which will remove sufficient lengths of the second resin layer 42 to allow contact of all the second thermoelement wires 43a–43n as shown in FIG. 6, or only a subset of the second thermoelement wires as illustrated in FIG. 9. Utilizing the techniques described in connection with FIGS. 6–9 and 10, it is possible to construct microtubing which can be utilized for a wide variety of temperature sensing applications.

Additionally, it must be added that in the electronic circuit diagram shown in FIG. 9, the second thermoelement wires 43 will be connected to a positive lead and the first thermoelement wire 41, or in the case of FIG. 10 first thermoelement wires 51a and 51b, will be connected to the negative lead. The polarity of the first and second thermocouple wires is only critical in the multiple thermocouple construction in order to be compatible and achieve the correct readings with general off-the-shelf thermocouple reading/measuring devices. Therefore, the first thermoelement wire 41 or the second thermoelement wire 43 could be connected to a positive lead with the other thermoelement wire connected to a negative lead.

Although there are numerous methods for attaching leads from a metering device to the first and second thermoelement wires 41 or 43, at least one method has been found to produce several advantages. There are several potential problems with connecting the thermoelement wires to leads. First, the first and second wires may be in close proximity to one another. Second, there may be difficulty in accessing these wires. Thirdly, strain relief must be taken into account to prevent wires from breaking when connecting the leads.

Figure 11:
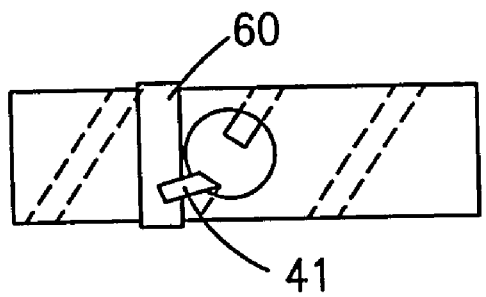
FIG. 11 is a side plan view of a section of microtubing with a thermoelement wire contacting a thermoelement band.
Figure 12:
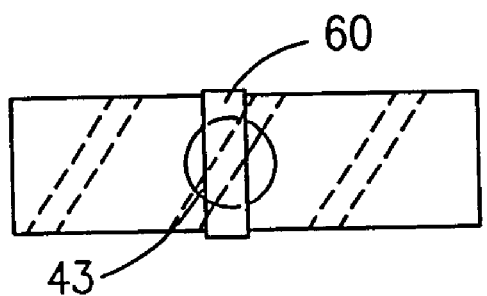
FIG. 12 is a side plan view of an alternatively preferred section of microtubing with a thermoelement wire contacting a thermoelement band.

The first step of this advantageous method is to expose the thermoelement wire 41 or 43 from the outer layer(s) of the microtubing by a process such as microblasting, or other mechanical or chemical machining process. Next a thermoelement band 60, shown in FIG. 11, is positioned over the catheter in proximity to the exposed thermoelement wire 41 or 43. At this point, the exposed wire may be clipped and/or bent and then welded to the thermoelement band 60. Alternatively, the thermoelement band 60 may be positioned so that a portion of the thermoelement band 60 is located atop the exposed thermoelement wire 41 or 43 (See FIG. 12). This process should be repeated for each wire that is utilized to form a thermocouple. The thermoelement band 60 is preferably constructed out of the same material that is utilized for that particular thermoelement wire 41 or 43 thereby producing a strain relief lead connection. If a material different than the thermoelement is used, a reference junction need not occur on the microtubing itself. The strain relief lead connections or reference junctions are typically formed at a proximal end of a section of microtubing 10. This method of attaching leads has been found to be effective at minimizing the profile of the microtube 10.

It will be understood that the manufacturing techniques of co-owned U.S. Pat. No. 5,888,436, may be utilized to achieve variations in microtubing size and flexibility over length and to impart other desirable structural characteristics as required for specific end uses.

Figure 13:
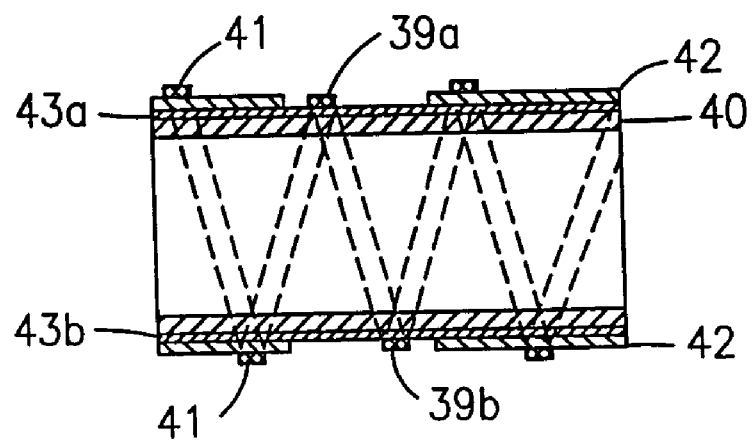
FIG. 13 is a sectional side plan view of a microtubing with two thermocouples spaced 180 degrees apart.

Finally, one particular embodiment which utilizes multiple thermocouples may be more fully illustrated in FIG. 13. This embodiment utilizes a first layer 40. Next, N second thermoelement wires 43a . . . 43n 360/N degrees apart are located on the exterior of the first layer 40. In FIG. 13, two second thermoelement wires 43a and 43b are utilized. Second layer 42 is then applied over the second thermoelement wires 43a . . . 43n. The second thermoelement wires 43a . . . 43n will be positive leads in the thermocouples.

Through selective removal, the second thermoelement wires 43a . . . 43n are exposed at a particular location. Next, a first thermoelement wire 41 is coiled around the tubing. This results in thermocouples 39a . . . 39n. In FIG. 13, thermocouples 39a and 39b are formed as there are two second thermoelement wires 43a, 43b utilized and one first thermoelement wire 41. Finally, the tubing is overcoated with a third layer 44 (not shown). This has been found effective at holding the wires in place.

While the invention has been described in terms of its preferred embodiments, numerous alterations of the products and methods herein described will suggest themselves to those skilled in the art. It will be understood that the details and arrangements of the embodiments that have been described and illustrated in order to explain the nature of the invention are not to be construed as any limitation of the invention, and all such alterations which do not depart from the spirit of invention are intended to be included within the scope of the appended claims.

We claim:

1. A microtubing with imbedded thermocouple comprising:
   an inner resin layer having a proximal end and a distal end and defining a lumen;
   a first thermoelement over the inner resin layer;
   a second resin layer over the first thermoelement, said second resin layer having a discontinues section wherein a portion of the first thermoelement remains uncovered;
   a second thermoelement over the second resin layer and in contact with said first thermoelement in the discontinues section to form a thermocouple joint; and
   a third resin layer over the second thermoelement and second resin layer.

2. The microtubing of claim 1 wherein the first thermoelement is bonded to the inner layer.

3. The microtubing of claim 1 wherein the first thermoelement is comprised of a wire selected from the group of iron, nickel chromium alloy, copper, tungsten, tungsten alloy, nickel chromium silicide, aluminum alloy, platinum rhenium alloy, or platinum rhodium alloy.

4. The microtubing of claim 1 wherein the second thermoelement is comprised of a wire selected from the group of copper-nickel alloy, nickel-aluminum alloy, tungsten alloy, platinum, platinum rhenium alloy, and platinum rhodium alloy, chromium alloy, or nickel silicide magnesium alloy.

5. The microtubing of claim 1 wherein the discontinues region is formed by chemical machining the second resin layer.

6. The microtubing of claim 1 wherein said third resin layer is of a darker color than the second resin layer.

7. The microtubing of claim 1 wherein the second resin layer is of a different color than the inner resin layer.

8. The microtubing of claim 1 wherein the lumen contains an element selected from the group of a guide wire, an optical fiber, a hypotube or an electrical conductor.

9. The microtubing of claim 1 wherein the outer diameter is less than about 0.09 inches.

10. The microtubing of claim 1 wherein the thickness of the tubing wall is less than about 0.01 inches.

11. The microtubing of claim 1 further comprising a strain relief lead connection located exterior to said third resin layer.

12. The microtubing of claim 1 wherein a temperature change at said thermocouple joint results in a time constant of less than 100 milliseconds.

13. The microtubing of claim 1 wherein said second thermoelement is in contact with said first thermoelement in at least two distinct locations within said discontinues section.

14. A microtubing with imbedded thermocouple compromising:
   an inner resin layer having a proximal end and a distal end and defining a lumen;
   a first thermoelement over the inner resin layer and connectable to a negative lead;
   a second resin layer over the first thermoelement, said second resin layer having at least one discontinues segment wherein a portion of the first thermoelement remains uncovered;
   a plurality of second thermoelements over the second resin layer and in contact with said first thermoelement, said second thermoelements being connectable to a positive lead; and
   a third resin layer over the second thermoelements and second resin layer.

15. The microtubing of claim 14 wherein the first thermoelement is bonded to the inner layer.

16. The microtubing of claim 14 wherein the second thermoelement is comprised of a wire selected from the group of iron, nickel chromium alloy, copper, tungsten, tungsten rhodium alloy, nickel chromium silicide alloy, nickel manganese silicon aluminum alloy, or platinum rhodium alloy.

17. The microtubing of claim 14 wherein the first thermoelement is comprised of a wire selected from the group of copper-nickel alloy, nickel-aluminum alloy, tungsten rhenium alloy, platinum, platinum rhodium alloy, nickel chromium alloy, or nickel silicide magnesium alloy.

18. The microtubing of claim 14 wherein the discontinues region is formed by chemical machining the second resin layer.

19. The microtubing of claim 14 wherein said third resin layer is of a darker color than the second resin layer.

20. The microtubing of claim 14 wherein the second resin layer is of a different color than the inner resin layer.

21. The microtubing of claim 14 wherein the lumen contains an element selected from the group of a guide wire, an optical fiber, a hypotube or an electrical conductor.

22. The microtubing of claim 14 wherein the outer diameter is less than about 0.09 inches.

23. The microtubing of claim 14 wherein the contact of one first thermoelement and N second thermoelements creates N thermocouple joints.

24. The microtubing of claim 14 wherein the contact of said first thermoelement and said second thermoelements creates thermocouple joints, said thermocouple joints being substantially evenly spaced from a proximal to a distal portion of said microtube.

25. The microtubing of claim 24 wherein the substantially even spacing of said thermocouple joints has an accuracy of within five percent.

26. The microtubing of claim 14 having N second thermoelements wherein said second thermoelements are spaced about 360/N degrees apart.

27. A microtube having an interior lumen comprising:
   at least one inner layer;
   a first thermoelement located on an exterior surface of said at least one inner layer;
   a second layer and at least one selected region, said second layer covering a portion of said at least one inner layer, said selected region located external to a portion of said at least one inner layer and above a portion of said first thermoelement;
   a portion of a second thermoelement located on an exterior surface of said second layer and another portion of said second thermoelement in contact with said first thermoelement forming a thermocouple joint; and
   a third layer covering said thermocouple and said portion of said second thermoelement located on said exterior surface of said second layer.

28. A process for manufacturing microtubing comprising the steps of:
   a) forming an inner layer;
   b) attaching a first thermoelement to said inner layer;
   c) applying a second layer over the first thermoelement;
   d) machining the second layer in a selected region to create a discontinuity in the second layer and expose a portion of the first thermoelement; and
   e) attaching a second thermoelement over the second layer and creating a thermocouple joint by contacting the first thermoelement in the discontinuity of the second layer; and f) applying a third layer over at least a portion of the second layer and thermocouple joint.

29. A microtubing with imbedded thermocouple comprising:

an inner resin layer having a proximal end and a distal end and defining a lumen;

a plurality of first thermoelements over the first resin layer and connectable to a positive lead;

a second resin layer over the plurality of first thermoelements, said second resin layer having at least one discontinues segment wherein a portion of the plurality of first thermoelements remains uncovered;

a second thermoelement over the second resin layer and in contact with said first thermoelements, said first thermoelement being connectable to a negative lead; and a third resin layer over the second thermoelement and second resin layer.

30. The microtubing of claim 29 wherein the first thermoelement is comprised of a wire selected from the group of iron, nickel chromium alloy, copper, tungsten, tungsten rhenium alloy, nickel chromium silicide alloy, nickel manganese silicon aluminum alloy, or platinum rhodium alloy.

* * * * *